United States Patent [19]

Lindigkeit

[11] Patent Number: 4,830,824

[45] Date of Patent: May 16, 1989

[54] DENTAL ALLOY CASTINGS AND METHOD

[75] Inventor: Jürgen Lindigkeit, Herne, Fed. Rep. of Germany

[73] Assignee: Fried. Krupp Gesellschaft mit beschrankter Haftung, Essen, Fed. Rep. of Germany

[21] Appl. No.: 27,973

[22] Filed: Mar. 19, 1987

[30] Foreign Application Priority Data

Mar. 19, 1986 [DE] Fed. Rep. of Germany ....... 3609184

[51] Int. Cl.$^4$ ............................................. C22C 19/07
[52] U.S. Cl. .................................... 420/436; 420/440; 433/207
[58] Field of Search ................ 420/436, 440; 148/425; 433/207

[56] References Cited

FOREIGN PATENT DOCUMENTS

| EP0041938 | 12/1981 | European Pat. Off. |
| EP0164329 | 11/1985 | European Pat. Off. |
| 2621789 | 8/1977 | Fed. Rep. of Germany. |
| 3300909 | 7/1984 | Fed. Rep. of Germany. |
| 3436118 | 5/1985 | Fed. Rep. of Germany. |
| WO85/04576 | 10/1985 | PCT Int'l Appl. |
| 2000188 | 1/1979 | United Kingdom. |

OTHER PUBLICATIONS

ISO 5832/IV-1978 (E), "Implants for Surgery—Metallic Materials—Part IV: Cobalt-Chromium-Molybdenum Casting Alloy", International Standard, p. 1.
ASTM Designation: F 75-82, "Standard Specification for Cast Cobalt-Chromium-Molybdenum Alloy for Surgical Implant Applications", pp. 13 to 14.
ASTM Designation: F 799 to 82, "Standard Specification for Thermomechanically Processed Cobalt--Chromium-Molybdenum Alloy for Surgical Implants", pp. 320-328.
Chemical Abstracts, vol. 98, 1983, 98:113670k.

Primary Examiner—R. Dean
Attorney, Agent, or Firm—Sughrue, Mion, Zinn, Macpeak, and Seas

[57] ABSTRACT

An alloy for producing dental castings comprises 26.5 to 27.5% Cr, 4.5 to 5.5% Mo, 0.65 to 0.8% Mn, 0.4 to 0.5% Si, up to 1% Fe, up to 0.05% C, and the balance Co.

6 Claims, No Drawings

DENTAL ALLOY CASTINGS AND METHOD

BACKGROUND OF THE INVENTION

The present invention relates to alloys which can be used for producing dental castings, to dental castings, and to methods for making dental castings.

It is known to use casting alloys of the CoCrMo type, as they are standardized internationally according to ISO 5832/IV and, for example, according to the ASTM-F-75 nationally in the U.S.A. for the production of surgical implants. Because of their compatibility with the body and their mechanical hardness as a material for endoprostheses, such as, for example, artificial hip and knee joints, alloys of this type have proven their value.

In general, however, special demands are placed on alloys which are utilized in the dental industry. For example, firing alloys for metal ceramics must be compatible with commercial dental ceramics with respect to thermal expansion and contraction. These alloys, moreover, must form an oxide layer of minimal thickness to ensure adhesion between metal and ceramic. Also, for aesthetic reasons, the oxide color must not show through the opaque ceramic. In the case of dental casting pieces that cannot be masked, for example, removable prostheses with clamps, a certain activation capability and elastic temper is demanded. Beyond this, in the dental industry it is especially important that processing of the alloys being used can be done with materials readily available in the dental laboratory, that is, one should be able to be cast them with the usual casting centrifuges. For this reason the alloys, those which heretofore have been used in the dental industry, and those used as model casting material, have a far higher C-content than is permitted by the standard mentioned earlier. Firing alloys used in the dental industry are based mainly on an NiCr basis when it is a question of alloys of a type extremely free of noble metals.

Also, there are already known firing alloys which are based on CoCr. Compare, for example, DE 34 36 118, DE 33 09 909 A1 and EP 0 041 938. These alloys, however do not satisfy the demands which, according to the standards mentioned above, are placed on materials for the production of surgical implants.

Thus, for example, the CoCrMo alloy according to EP 0 041 938 contains 0.1 to 0.25% C, 0.1 to 3% Si and 0.1 to 8.0% Mn, where the high Mn and Si content levels are supposed to improve flow behavior. These high content levels are, however, not desirable in materials used in the production of surgical implants, that is, materials with which the present invention concerns itself. The alloy according to EP 0 041 938 contains 25 to 35 (preferably 27 to 33) % Cr, 3 to 8 (preferably 4 to 7) % Mo, up to 1% Fe, up to 0.3 (preferably up to 0.2) % Ni, and the remainder Co.

DE 33 00 909 discloses an alloy containing 0 to 0.3% C, 1 to 2% Si, 0 to 1.5% Mn, 20 to 35% Cr, 2 to 8% Mo, 0.3 to 2% Fe, 0.3 to 1.5% of Cer and/or Yt, and balance Co.

DE 34 36 118 discloses an alloy containing up to 2% C, 60 to 70% Co, 25 to 30% Cr and 3 to 7% Mo.

SUMMARY OF THE INVENTION

An object of the present invention is to provide a dental casting which can be readily cast in conventional casting centrifuges.

A further object of the present invention is to provide a dental casting which has a thermal coefficient of expansion which is compatible with commercial dental ceramics.

Another object of the present invention is to provide a dental casting which has a small carbon content, but which nevertheless has a satisfactory flow behavior during casting.

Another object of the present invention is to provide a dental casting which has a hardness corresponding to the hardness of natural tooth enamel and which has a satisfactory oxide layer.

A still further object of the present invention is to provide a casting alloy which can be used to make such dental castings and to provide a method of making dental castings.

Additional objects and advantages of the present invention will be set forth in part in the description which follows and in part will be obvious from the description or can be learned by practice of the invention. The objects and advantages are achieved by means of the compositions, processes, instrumentalities and combinations particularly pointed out in the appended claims.

To achieve the foregoing objects and in accordance with its purpose, the present invention provides a CoCrMo casting alloy which contains 26.5 to 27.5% Cr, 4.5 to 5.5% Mo, 0.65 to 0.8% Mn, 0.4 to 0.5% Si, up to 1% Fe, up to 0.05% C, and the balance Co. As used throughout the specification and claims, the percents are weight percents unless otherwise noted.

The present invention rests upon the surprising discovery that the above alloy is suited for producing casting parts for dental needs. It was surprising here not only that the alloy demonstrates satisfactory flow behavior in spite of its small carbon content, but it has a thermal coefficient of expansion of from $14.5 \times 10^{-6} K^{-1}$ to $15.5 \times 10^{-6} K^{-1}$, which is compatible with available dental ceramics. It was also found that the alloy of the present invention forms a satisfactory oxide layer which contributes to compound firmness and strength of up to 42N in impact testing under the german standard DIN 51.155. Finally, it has been seen that from the alloys of the present invention, even the most delicate and thin-walled castings parts may be produced, as frequently encountered in dental science.

Preferably, the ratio of Mn to Si in the alloy is between 1.6:1 and 1.7:1. It is also preferred that the alloy has an Ni content between 0.05 and 0.2%. The alloy generally comprises, consists essentially of, or consists of the recited elements.

It is to be understood that both the foregoing general description and the following detailed description are exemplary and explanatory, but are not restrictive of the invention.

DETAILED DESCRIPTION OF THE INVENTION

An alloy with a composition of 26.5 to 27.5% Cr, 4.5 to 5.5% Mo, 0.65 to 0.8% Mn, 0.4 to 0.5% Si, up to 1% Fe, up to 0.05% C, an Mn to Si ratio between 1.6:1 and 1.7:1 and the balance Co is cast in an inductively heated laboratory casting centrifuge and the following values are attained:

0.2% Yield Stength: $R_{p\ 0.2} = 515$ N/mm$^2$
Tensile Strength: $R_m = 740$ N/mm$^2$
Elongation at Rupture: $A_5 = 18\%$ The hardness, surprisingly low for cobalt-chrome alloys, in the cast condition amounts to 300 to 330 HV 10 (Vickers hardness 10). It thus corresponds to about the hardness of natural tooth enamel, and, as the hardness values are comparable, it can therefore be assumed that a dental casting made from this alloy will not abrasively wear the tooth enamel down, as occurs with harder crown and bridge materials. Nor is it to be expected that the chewing surface of crowns or bridges produced from the alloys according to the present invention will be deformed by the materials which ordinarily come in contact with these surfaces, in contrast to the deformation that can occur when soft materials are used as dental castings. A further advantage of the alloy of the present invention is its low Ni content. This means that even patients who are allergic to Ni, who wear prostheses produced from these alloys, do not have to expect ill-effects. An other alloy with a composition of Cr 27,1%, Mo 5,16%, Mn 0,69%, Si 0,43%, Ni 0,07%, Fe 0,19%, C 0.015% and rest Co is cast also in an inductively heated laboratory casting centrifuge and the following values are attained 0.2% Yield Strength: $R_{p\ 0.2} = 515\ N/mm^2$
Tensile Strength: $R_m = 740\ N/mm^2$
Elongation at Rupture: $A_5 = 18\%$ It will be understood that the above description of the present invention is susceptible to various modifications, changes and adaptations, and the same are intended to be comprehended within the meaning and range of equivalents of the appended claims.

What is claimed is:

1. A dental casting comprised of an alloy consisting essentially of 26.5 to 27.5% Cr, 4.5 to 5.5% Mo, 0.65 to 0.8% Mn, 0.4 to 0.5% Si, up to 1% Fe, up to 0.05% C, and the balance Co.

2. The dental casting according to claim 1, wherein the alloy has a ratio of Mn to Si of between 1.6:1 and 1.7:1.

3. The dental casting according to claim 1, wherein the alloy has an Ni content of 0.05 to 0.2%.

4. A method of forming a dental casting into a dental form comprising: casting an alloy which consisting essentially of 26.5 to 27.5% Cr, 4.5 to 5.5% Mo, 0.65 to 0.8% Mn, 0.4 to 0.5% Si, up to 1% Fe, up to 0.05% C, and the balance Co.

5. The method according to claim 4, wherein the alloy has a ratio of Mn to Si of between 1.6:1 to 1.7:1.

6. The method according to claim 4, wherein the alloy has an Ni content of 0.05 to 0.2%.

* * * * *